(12) United States Patent
Yang et al.

(10) Patent No.: US 11,692,221 B2
(45) Date of Patent: Jul. 4, 2023

(54) NUCLEIC ACID SEQUENCING METHOD

(71) Applicants: MGI TECH CO., LTD., Shenzhen (CN); COMPLETE GENOMICS, INC., San Jose, CA (US)

(72) Inventors: Jin Yang, Shenzhen (CN); Xun Xu, Shenzhen (CN); Hui Wang, Shenzhen (CN); Bin Xie, Shenzhen (CN); Zhuokun Li, Shenzhen (CN); Shengming Zhao, Shenzhen (CN); Ao Chen, Shenzhen (CN); Chongjun Xu, San Jose, CA (US); Wenwei Zhang, Shenzhen (CN); Ming Ni, Shenzhen (CN)

(73) Assignees: MGI TECH CO., LTD., Guangdong (CN); COMPLETE GENOMICS, INC., San Jose, CA (US)

( * ) Notice: Subject to any disclaimer, the term of this patent is extended or adjusted under 35 U.S.C. 154(b) by 450 days.

(21) Appl. No.: 16/635,131

(22) PCT Filed: Aug. 1, 2017

(86) PCT No.: PCT/CN2017/095520
§ 371 (c)(1),
(2) Date: Jan. 29, 2020

(87) PCT Pub. No.: WO2019/023951
PCT Pub. Date: Feb. 7, 2019

(65) Prior Publication Data
US 2020/0318177 A1  Oct. 8, 2020

(51) Int. Cl.
*C12Q 1/6869* (2018.01)
*C12Q 1/6876* (2018.01)
*G01N 21/64* (2006.01)

(52) U.S. Cl.
CPC ......... *C12Q 1/6869* (2013.01); *C12Q 1/6876* (2013.01); *G01N 21/6486* (2013.01); *B01L 2200/10* (2013.01)

(58) Field of Classification Search
CPC .. C12Q 1/6889; C12Q 1/6876; C12Q 1/6874; G01N 21/6486
See application file for complete search history.

(56) References Cited

U.S. PATENT DOCUMENTS

| 5,817,464 A | 10/1998 | Kambara et al. |
| 2006/0234371 A1 | 10/2006 | Shirazi |
| 2010/0111768 A1* | 5/2010 | Banerjee ............ G01N 21/6456 422/82.08 |

FOREIGN PATENT DOCUMENTS

| CN | 1106459 A | | 8/1995 |
| CN | 101189345 A | | 5/2008 |
| CN | 103993100 A | | 8/2014 |
| WO | WO 9106678 | * | 10/1990 |
| WO | WO 00/18957 A1 | | 4/2000 |
| WO | WO 2006/084132 A2 | | 8/2006 |
| WO | WO 2007/120208 A2 | | 10/2007 |
| WO | WO 2007/121489 A2 | | 10/2007 |

OTHER PUBLICATIONS

Fehlmann et al., Clinical Epigenetics, vol. 8: 123, 1-11, (Year: 2016).*
Mir et al., "Sequencing by Cyclic Ligation and Cleavage (CycLiC) directly on a microarray captured template", Nucleic Acids Research, 2009, 37(1): e5.
Nunez et al., "A Cost-Effective Approach to Sequence Hundreds of Complete Mitochondrial Genomes", PLoS One, 2016, 11(8): e0160958.
Seo et al., "Four-color DNA sequencing by synthesis on a chip using photocleavable fluorescent nucleotides", PNAS, 2005, 102(17): 5926-5931.

* cited by examiner

*Primary Examiner* — Cynthia B Wilder
(74) *Attorney, Agent, or Firm* — James S. Keddie; Bozicevic, Field & Francis LLP (57) ABSTRACT

The present invention provides a method for sequencing a nucleic acid using an immersion reaction protocol. The immersion reaction protocol comprises sequentially immersing a solid support having nucleic acid molecules immobilized thereon in different reaction containers to realize nucleic acid sequencing.

19 Claims, 3 Drawing Sheets

NUCLEIC ACID SEQUENCING METHOD

CROSS-REFERENCE TO RELATED APPLICATIONS

This application is a § 371 national phase of International Application No. PCT/CN2017/095520, filed on Aug. 1, 2017, which application is incorporated by reference herein.

TECHNICAL FIELD

The present invention pertains to a field of nucleic acid sequencing. Specifically, the present invention relates to a method for sequencing a nucleic acid by using an immersion reaction protocol, in which the immersion reaction protocol comprises sequentially immersing a solid support having nucleic acid molecules immobilized thereon in different reaction containers to realize nucleic acid sequencing.

BACKGROUND ART

The second-generation sequencing technology is developed based on the first-generation Sanger sequencing technology, and has features of low cost, high throughput, and automation, and the like. It has greatly promoted the development of the gene sequencing industry. Recently, the second-generation sequencing technology has been widely used in whole genome sequencing, transcriptome sequencing and metagenome sequencing, etc., is a powerful tool for analyzing evolution and classification of organisms, studying genes associated with diseases such as cancers and autism and the like, and conducting in vitro diagnostics, etc., and promotes further understanding of life sciences and the development of health industry.

The existing second-generation sequencing technologies mainly include SBS technology (Sequencing-by-Synthesis) from Illumina, semiconductor sequencing technology from Life Technologies, and combinatorial probe-anchor synthesis technology (cPAS) from BGI. In the SBS technology, dNTPs (i.e., dATP, dCTP, dGTP, dTTP) with two modified moieties (fluorescent label and blocking group) are used, in which each of dATP, dCTP, dGTP and dTTP carries different fluorescent labels. Due to the presence of a blocking group, only one complementary dNTP is added to each nucleic acid template during the polymerization reaction. Thus, the identity of the added complementary dNTP can be determined by detecting the fluorescent label carried by the dNTP. The reversible blocking group and fluorescent label can be removed subsequently by reagents (known as a regeneration reaction) so as to perform next polymerization reaction (P085, Genomics, First Edition, 2016, edited by Yang Huanming). In the semiconductor sequencing technology, the change in pH caused by pyrophosphate released by dNTP polymerized during template chain extension is used, and this change is detected by sensors at the bottom of chip to obtain sequence information of DNA chain (P083, Genomics, First Edition, 2016, edited by Yang Huanming) The second-generation sequencing technology protocol SOLiD developed by ABI company (USA) uses SBL method (Sequencing-by-Ligation) for high-throughput sequencing. The SBL method of SOLiD uses a mixture of a ligase and 8-base single-stranded fluorescent probes, which can be combined with the circular ligation of different primers to achieve a read length between 35 and 70 nt, and its advantage is high accuracy (P093, Genomics, First Edition, 2016, edited by Yang Huanming) The combinatorial probe-anchor synthesis (cPAS) uses a DNA molecular anchor and a fluorescent probe to perform polymerization on DNA nanospheres (DNB), and then a high-resolution imaging system collects optical signals, and the sequence to be tested can be obtained after digital processing of the optical signals; in which the DNB enhances the signal by linear amplification so as to reduce the error rate of single copy (see BGISEQ-500 sequencing platform).

The biochemical reaction part of the existing second-generation sequencing technology is mainly carried out by using a flow channel system. A typical flow channel system can be found in WO2007123744, which uses a solid substrate including a flow cell, wherein the flow cell includes one or more fluid channels to which a polynucleotide is attached, and a fluorescently labeled reagent can be controlled by a flow guide system to flow through the fluid channel to contact the polynucleotide. For example, Illumina's HiSeq 2500 platform uses a flow cell, the sequencing reaction reagents are pumped from a refrigeration device to the flow cell at a specific position and a specific time and flow through sequencing chip under control of a complex set of fluid control equipment and under assistance of a sophisticated temperature control facility, so that the biochemical reaction is ensured to be sufficiently performed in a time period as short as possible (HiSeq® 2500 System Guide, Illumina, 2015).

The existing second-generation sequencing methods require precise temperature control and fluid control, have higher cost, and are prone to occurrence of nonuniform reactions. The reagents are disposable and have low utilization rate, which further increase sequencing cost. The existing second-generation sequencing platforms such as HiSeq 2500 and the like that use flow channel protocol still have low throughput, that is, the throughput of each unit is less than 1 WGS/day (referring to www.illumina.com.cn/systems/hiseq_2500_1500/performance_specifications.html).

Therefore, there is an urgent need in the art for new high-throughput, low-cost second-generation sequencing methods.

DESCRIPTION OF INVENTION

Aiming at the problems in the existing second-generation sequencing methods, the present invention provides a method for sequencing a nucleic acid using an immersion reaction protocol, in which the immersion reaction protocol comprises sequentially immersing a solid support having nucleic acid molecules immobilized thereon in different reaction containers to perform nucleic acid sequencing. The term "immersion reaction protocol" as used herein is mentioned with respect to the flow channel system used in the prior art, which means that during the nucleic acid sequencing, the nucleic acid to be sequenced is moved to contact each reaction reagent, rather than the reaction reagent is moved by a flow channel to contact the nucleic acid. The immersion reaction protocol has at least the following advantages: 1) reuse of biochemical reagents; 2) good scalability, flexible usage, and capability of greatly increasing the throughput; 3) no requirement for a complicated system for controlling temperature and fluid, and better uniformity of reaction; and 4) significant reduction in cost of gene sequencing.

In the method described herein, the nucleic acid sequencing can be performed using a variety of sequencing methods. Examples of the sequencing methods include, but are not limited to, electrophoresis, sequencing-by-synthesis, sequencing-by-ligation, sequencing by combinatorial probe-anchor synthesis, sequencing-by-hybridization, single molecule sequencing, and real-time sequencing methods. In some embodiments, the process of determining the nucleotide sequence of a target nucleic acid can be an automated process.

It should be understood that any sequencing process can be incorporated into the method described herein. In addition, it should be understood that other known sequencing processes can be easily implemented and used in the method described herein.

Therefore, in one embodiment, the present invention provides a method for sequencing a nucleic acid using an immersion reaction protocol, wherein the immersion reaction protocol comprises the following steps:

a) providing a first batch of solid supports having nucleic acid molecules immobilized thereon, b) immersing the first batch of solid supports in one or more reaction solutions to generate a signal representing a nucleotide sequence of the nucleic acid molecule on the solid supports, wherein each of the one or more reaction solutions is placed in a separate reaction container, wherein, after removing the first batch of solid supports from each of the reaction solutions, washing the first batch of solid supports to remove the reaction solution remaining on the solid supports, c) detecting the signal on the first batch of solid supports, d) immersing the first batch of solid supports in a regeneration solution placed in another reaction container to eliminate the signal on the solid supports, e) removing the first batch of solid supports from the regeneration solution, and washing the first batch of solid supports to remove the regeneration solution remaining on the solid supports, and f) optionally, repeating the steps b) to e) or the steps b) to c).

In one embodiment, the steps b) to e) may be repeated one or more times, such as 1, 2, 3, 4, 5, 10, 15, 20, 30, 40, 50, 60, 70, 80, 90, 100 or more times.

In certain embodiments, the washing is performed by immersing the solid support in a reaction container containing a washing solution.

As used herein, the immersing comprises any means of bringing all nucleic acid molecules immobilized on the solid support into contact with the reagents or solution in the reaction container. The solid support may be partially or fully immersed in the reaction container, for example, in a vertical, inclined or horizontal manner, provided that all the nucleic acid molecules immobilized on the solid support are in contact with the reagents in the reaction container.

As used herein, the "nucleic acid molecule" to be sequenced can be any type of nucleic acid, for example, the nucleic acid can be deoxyribonucleic acid (DNA), ribonucleic acid (RNA), or an analog of DNA or RNA made from a nucleotide analog, and this term can be used interchangeably with "polynucleotide". The nucleic acid can be single-stranded, double-stranded, or contain both single- and double-stranded sequences. The nucleic acid molecule may be derived from a double-stranded DNA (dsDNA) form (e.g., genomic DNA, PCR, amplification products, etc.), or may be derived from a single-stranded form such as DNA (ssDNA) or RNA and may be converted into a dsDNA form, and vice versa. In some embodiments, the nucleic acid to be sequenced can be in the form of a single molecule (which can be a natural molecule, a modified molecule such as a labeled molecule, or a nucleic acid comprising a nucleotide analog), a concatemer of sequence (e.g., a DNA nanosphere, etc.), can be amplified (e.g., amplified into a concatemer, amplified into a plurality of individual molecules having same or similar sequences, etc.), and/or can be in any other form. The exact sequence of the nucleic acid molecule may be known or unknown. The illustrative examples of nucleic acids are as follows: genes or gene fragments (e.g., probes, primers, EST or SAGE tags), genomic DNA, genomic DNA fragments, exons, introns, a messenger RNA (mRNA), transit RNA, a ribosomal RNA, a ribozyme, cDNA, a nucleic acid library, recombinant polynucleotides, synthetic polynucleotides, branched polynucleotides, plasmids, vectors, an isolated DNA of any sequence, an isolated RNA of any sequence, and nucleic acid probes, primers or amplified copies of any of the above sequences.

The nucleic acid can comprise nucleotides or nucleotide analogs. The nucleotide usually comprises a ribose, a nucleobase, and at least one phosphate group. The nucleotide can be base-free (i.e., absence of nucleobase). The nucleotides comprise deoxyribonucleotides, modified deoxyribonucleotides, ribonucleotides, modified ribonucleotides, peptide nucleotides, modified peptide nucleotides, modified phosphate saccharide backbone nucleosides, and mixtures thereof. Examples of nucleotides include, for example, adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP). The nucleotide analogs comprising modified nucleobases can also be used in the method described herein. Whether having a natural backbone or a similar structure, exemplary modified nucleobases that can be comprised in a polynucleotide include, for example, inosine, xanthine, hypoxanthine, isocytosine, isoguanine, 2-aminopurine, 5-methylcytosine, 5-hydroxymethylcytosine, 2-aminoadenine, 6-methyladenine, 6-methylguanine, 2-propylguanine, 2-propyladenine, 2-thiouracil, 2-thiothymine, 2-thiocytosine, 15-halouracil, 15-halocytosine, 5-propynyluracil, 5-propynylcytosine, 6-azouracil, 6-azocytosine, 6-azothymine, 5-uracil, 4-thiouracil, 8-halo adenine or guanine, 8-amino adenine or guanine, 8-thio adenine or guanine, 8-thioalkyl adenine or guanine, 8-hydroxy adenine or guanine, 5-halogen-substituted uracil or cytosine, 7-methylguanine, 7-methyladenine, 8-azaguanine, 8-azaadenine, 7-deazaguanine, 7-deazaadenine, 3-deazaguanine, 3-deazaadenine, and the like. As is known in the art, certain nucleotide analogs, for example, nucleotide analogs, such as adenosine 5'-phosphoryl sulfate, cannot be incorporated into a polynucleotide.

The nucleic acid molecule to be sequenced in specific embodiments of the invention can be of any length. In general, exemplary lengths of useful nucleic acids include, for example, at least about 5, 10, 20, 30, 40, 50, 60, 70, 80, 90, 100, 150, 200, 300, 400, 500, 1,000, 5,000 or 10,000, 100,000 nucleotides or longer. Alternatively, or in addition, the length may be no longer than 1,000,000, 100,000, 10,000, 1,000, 100 nucleotides or less. The length of the nucleic acid molecule may also include all integers between the above exemplary numbers. Thus, the nucleic acid that can be sequenced using the method described herein can, for example, be within the scope of short polynucleotides, fragments, cDNAs, genes, and genomic fragments.

The number of the nucleic acid molecules to be sequenced in a specific embodiment of the present invention can be any number, for example, it can be 2, 3, 4, 5, 6, 7, 8, 9, 10, 20, 30, 40, 50, 60, 70, 80, 90, or 100 or more identical or different nucleic acid molecules. The number of nucleic acid molecules to be sequenced can also be, for example, 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, or $1\times10^7$ or more identical or different nucleic acid molecules. The number of nucleic acid molecules to be sequenced may also include all integers between the above exemplary numbers.

The nucleic acids can be obtained from any source. For example, the nucleic acid can be prepared from a nucleic acid molecule obtained from one organism, or from a population of nucleic acid molecules obtained from a natural source including one or more organisms. The sources of nucleic acid molecules include, but are not limited to, organelles, cells, tissues, organs, or organisms. The cells that can be used as a source of nucleic acid molecules can be prokaryotic (e.g., bacteria); or eukaryotic, such as fungi (e.g., yeast), plants, protozoa, and other parasites, and animals (including insects, nematodes), and mammals (e.g., rat, mouse, monkey, non-human primate, and human); or the nucleic acid molecule may be derived from a virus.

In some embodiments, the nucleic acid can be obtained from a particular biological source. In a preferred embodiment, the nucleic acid is a human nucleic acid obtained from a human, for example, a sample of human tissue. In another preferred embodiment, the nucleic acid is a human mitochondrial nucleic acid. In another preferred embodiment, the nucleic acid can be obtained from a metagenomic sample. In other embodiments, the nucleic acid can be obtained from an environmental source that no longer contains a living organism.

As used herein, the term "immobilized" means direct or indirect attachment to a solid support via a covalent or non-covalent bond. In certain embodiments of the present disclosure, a covalent attachment may be used, but what is required is generally only that the nucleic acid is stably immobilized or attached to a solid support under a condition desirable to use a solid support (e.g., in an application requiring nucleic acid amplification and/or sequencing). Generally, an oligonucleotide to be used as a capture primer or an amplification primer (for example, a primer having a partially double-stranded structure of the present invention) is immobilized such that the 3' end is available for enzymatic extension and at least a portion of the primer sequence is capable of hybridizing to a complementary nucleic acid sequence. The immobilization can occur via hybridization to a surface-attached oligonucleotide, in which case the immobilized oligonucleotide or polynucleotide can be in 3'-5' direction. Another way of non-covalent attachment may be to bind a nucleic acid binding protein to a solid support by amino modification and capture the nucleic acid molecule through the nucleic acid binding protein. Alternatively, the immobilization may occur by means other than base-pairing hybridization, such as the covalent attachment described above. Non-limiting examples of the method for attachment of the nucleic acid to the solid support include nucleic acid hybridization, biotin streptavidin binding, thiol binding, photoactivation binding, covalent binding, antibody-antigen, physical confinements via hydrogel or other porous polymers, etc. Various exemplary methods for immobilizing the nucleic acid on the solid support can be found, for example, in G. Steinberg-Tatman et al., Bioconjugate Chemistry 2006, 17, 841-848; Xu X. et al. Journal of American Chemical Society 128 (2006) 9286-9287; U.S. patents or applications U.S. Pat. Nos. 5,639,603, 5,641,658, US2010248991; international patent applications WO2001062982, WO2001012862, WO2007111937, and WO0006770; for all purposes, especially for all relevant teachings of the preparation of solid supports with nucleic acids immobilized thereon, the above documents are incorporated herein by reference in their entirety.

As used herein, the term "solid support" refers to any insoluble substrate or matrix to which the nucleic acid can be attached, such as, for example, latex beads, dextran beads, polystyrene surfaces, polypropylene surfaces, polypropylene amide gels, gold surfaces, glass surfaces, chips, sensors, electrodes, and silicon wafers. The surface of the solid support may be of any desired shape, and the shape includes, for example, planar, spherical or porous shape suitable for a particular application. For example, the solid support may be a flat glass surface. The solid support can also be installed inside a flow cell to allow interaction with a solution of multiple reagents.

In certain embodiments, the solid support may include an inert substrate or matrix, and the inert substrate or matrix has been chemically functionalized, for example, by applying an intermediate material layer or coating, and the intermediate material has reactive groups allowing covalent attachment to a polynucleotide. The intermediate material may be directly or indirectly attached to the solid support via a covalent or non-covalent bond. As a non-limiting example for non-covalent attachment to a solid support, this type of support may comprise a polyacrylamide hydrogel layer on an inert substrate such as glass. In such embodiments, the polynucleotide may be directly covalently attached to an intermediate layer (e.g., a hydrogel), but the intermediate layer itself may be non-covalently attached to another substrate or matrix (e.g., a glass substrate) layer.

As used herein, the term "reaction container" refers to any device capable of containing a reaction solution, including but not limited to tank, canal, well, test tube, cup, dish, and the like. The reaction container may have any suitable shape, for example, the reaction container may be of square, spherical, conical, cylindrical, irregular shape, etc. The reaction container may have any suitable size, for example, its size can be adjusted arbitrarily according to the volume of reaction solution to be accommodated, for example, it may have a size capable of accommodating at least 1 µL, at least 5 µL, at least 10 µL, at least 20 µL, at least 50 µL, at least 100 µL, at least 1 mL, at least 5 mL, at least 10 mL, at least 20 mL, at least 50 mL, at least 100 mL, at least 200 mL, at least 500 mL, at least 1 L or more of the reaction solution, or a size capable of accommodating at most 1 µL, at most 5 µL, at most 10 µL, at most 20 µL, at most 50 µL, at most 100 µL, at most 1 mL, at most 5 mL, at most 10 mL, at most 20 mL, at most 50 mL, at most 100 mL, at most 200 mL, at most 500 mL, at most 1 L or more of the reaction solution. The reaction container may be made of any suitable material, for example, glass, metal such as stainless steel, polymeric material such as plastic, and the like. It should be understood that the material of the reaction container should not adversely affect the reactivity of the reaction solution.

As used herein, the term "reaction solution" refers to reagents used in any sequencing method suitable for use in the immersion reaction protocol described herein. As described herein, such sequencing methods may include, but are not limited to, sequencing-by-electrophoresis, sequencing-by-synthesis, sequencing-by-ligation, sequencing by combinatorial probe-anchor synthesis, sequencing-by-hybridization, single molecule sequencing, and real-time sequencing methods. Therefore, the one or more reaction solutions used in the step b) and the regeneration solution used in the step d) of the immersion reaction protocol of the present invention depend on the sequencing method as used. It is within the capability of those skilled in the art to determine the one or more reaction solutions used in the step b) and the regeneration solution used in the step d) of the immersion reaction protocol of the present invention according to the sequencing method.

Accordingly, in a specific embodiment, the present invention relates to a method for sequencing-by-ligation of a nucleic acid molecule using the immersion reaction protocol as described herein. In such an embodiment, the one or more reaction solutions of step b) comprise a reagent for generating a ligation product on the nucleic acid molecule to be sequenced and generating a signal representing a nucleotide sequence of the nucleic acid molecule to be sequenced in the sequencing-by-ligation, and the regeneration solution of step d) comprises a reagent for eliminating the signal from the nucleic acid molecule to be sequenced and enabling the initiation of the next sequencing-by-ligation reaction.

The sequencing-by-ligation as used herein can be any of a variety of sequencing-by-ligation methods well known in the art. Basically, the sequencing-by-ligation involves hybridization and ligation of a labeled (e.g., fluorescently labeled) sequencing probe and an anchor probe (also known as "primer" in SOLiD sequencing) to a DNA strand. The sequencing probe comprises one or two intrinsically known sequencing bases (single-base sequencing probes or two-base sequencing probes) and a series of degenerate or universal bases, which allow complementary pairing between the sequencing probe and the nucleic acid template. The anchoring probe sequence is a known sequence which is complementary to an adaptor sequence on a nucleic acid template (the adaptor sequence means an oligonucleotide whose sequence is known in the nucleic acid template) and provides a site for initial ligation. After ligation, the template is imaged and the one or two known bases in the sequencing probe are identified. After the anchor probe-sequencing probe complex has been completely removed or the label (such as a fluorophore) has been removed by cleavage and the ligation site is regenerated, the next sequencing-by-ligation cycle begins.

Thus, in one embodiment of the sequencing-by-ligation of a nucleic acid molecule using the immersion reaction protocol described herein, the one or more reaction solutions of the step b) comprise a solution containing an anchor probe, a labeled (e.g., fluorescently labeled) sequencing probe, a ligase, or a mixture thereof, provided that the solid support is in contact with each of the anchor probe, the labeled sequencing probe and the ligase, wherein the signal on the solid support is generated by the labeled sequencing probe that complementarily binds to the nucleic acid molecule on the solid support, the labeled sequencing probe is linked via the ligase to the anchor probe that complementarily binds to the same nucleic acid molecule. In another embodiment of the sequencing-by-ligation of nucleic acid molecule using the immersion reaction protocol described herein, prior to the step b), the solid support with nucleic acid molecules immobilized thereon is allowed to contact with the anchor probe (also known as "primer" in SOLiD sequencing), so that the anchoring probe hybridizes to the nucleic acid molecule on the solid support, and the one or more reaction solutions of the step b) comprise a solution containing a labeled (e.g., fluorescently labeled) sequencing probe, a ligase, or a mixture thereof, provided that the solid support is in contact with either of the labeled sequencing probe and the ligase, and wherein the signal on the solid support is generated by the labeled sequencing probe that complementarily binds to the nucleic acid molecule on the solid support, the labeled sequencing probe is linked via the ligase to the anchor probe that complementarily binds to the same nucleic acid molecule.

The specific composition of the one or more reaction solutions in the step b) varies depending on the specific sequencing-by-ligation method as used. For example, when a single anchored probe is used, the one or more reaction solutions of the step b) may comprise only one reaction solution, wherein the reaction solution comprises a ligase and a labeled sequencing probe, optionally, also comprises an anchor probe; alternatively, the one or more reaction solutions of the step b) may also comprise two reaction solutions, wherein, one of the reaction solutions comprises an anchor probe and the other reaction solution comprises a labeled sequencing probe, and at least one of these two reaction solutions comprises a ligase, and thus, in this case, the step b) comprises the following process: immersing the solid support in the reaction solution containing the anchor probe, washing, and then immersing in the reaction solution containing the labeled sequencing probe, and washing. Alternatively, the one or more reaction solutions of the step b) may further comprise three reaction solutions, each of which comprises an anchor probe, a labeled sequencing probe, and a ligase, respectively; and in such a case, the step b) comprises the following process: immersing the solid support in the reaction solution containing the anchor probe and washing, then immersing in the reaction solution containing the labeled sequencing probe and washing, and then immersing in the reaction solution containing the ligase and washing. Similarly, in the case of using dual anchor probes, the one or more reaction solutions of the step b) may comprise only one reaction solution simultaneously containing a ligase, a first anchor probe, a second anchor probe, and a labeled sequencing probe, or a plurality of reaction solutions each containing a ligase, a first anchor probe, a second anchor probe, a labeled sequencing probe, or a mixture thereof.

For the description about the sequencing-by-ligation, especially about the anchor probes and sequencing probes, the references can be made in WO2013066975, U.S. Patent Nos. 60/992,485, 61/026,337, 61/035,914 and 61/061,134. The detailed description of the sequencing-by-ligation can also be found in, for example, Landegren, U., Kaiser, R., Sanders, J. & Hood, L. A ligase-mediated gene detection technique. Science 241, 1077-1080 (1988), U.S. Pat. Nos. 6,969,488, 6,172,218, and 6,306,597 (the disclosures thereof are incorporated herein by reference in their entirety). In a preferred embodiment, the sequencing-by-ligation comprises sequencing by combinatorial probe-anchor ligation (cPAL) (see the description of WO2013066975).

As used herein, the term "ligase" refers to a nucleic acid modifying enzyme that catalyzes formation of intramolecular and intermolecular phosphodiester bonds between 5'-phosphate and 3'-hydroxy termini of nucleic acid chain. The ligase can be obtained from recombinant or natural sources. One or more low temperature (e.g., room temperature or lower) ligases (e.g., T3 DNA ligase, T4 DNA ligase, T7 DNA ligase, and/or *E. coli* DNA ligase) can be used. The ligase may also be a thermostable ligase. Thermostable ligases from thermophiles can be used. Examples of thermostable DNA ligase include, but are not limited to: Tth DNA ligase (from *Thermus thermophilus*, which is available from, for example, Eurogentec and GeneCraft); Pfu DNA ligase (a hyperthermophilic ligase from *Pyrococcus furiosus*); Taq ligase (from *Thermus aquaticus*), and any other suitable thermostable ligases, or any combination thereof.

In another specific embodiment, the present invention relates to a method of sequencing-by-synthesis of a nucleic acid molecule by using the immersion reaction protocol described herein. In such an embodiment, the one or more reaction solutions of the step b) comprise a reagent for carrying out a polymerization reaction using a nucleic acid molecule to be sequenced as a template in the sequencing-by-synthesis and generating a signal representing a nucleotide sequence of the nucleic acid molecule, and the regeneration solution of the step d) contains a reagent for eliminating the signal from the nucleic acid molecule to be sequenced and enabling the initiation of the next sequencing-by-synthesis reaction.

The sequencing-by-synthesis as used herein can be any of a variety of sequencing-by-synthesis methods well known in the art. Basically, the sequencing-by-synthesis involves firstly hybridizing a nucleic acid molecule to be sequenced with sequencing primers, and then polymerizing a labeled (e.g., fluorescently labeled) nucleotide at 3' end of the sequencing primers with the nucleic acid molecule to be sequenced as a template in the presence of a polymerase. After polymerization, the labeled nucleotide is identified by detecting the label. After removing the label (such as fluorophore) from the labeled nucleotide, the next sequencing-by-synthesis cycle begins. In one embodiment, the nucleic acid molecule to be sequenced is immobilized on a solid support by hybridizing to sequencing primers immobilized on the solid support. In another embodiment, in the immersion reaction protocol of the present invention, the solid support having nucleic acid molecules immobilized thereon is contacted with the sequencing primers before the step b), so that the sequencing primers hybridize to the nucleic acid molecule on the solid support.

Thus, in one embodiment of performing sequencing-by-synthesis of a nucleic acid molecule by using the immersion reaction protocol described herein, the one or more reaction solutions of the step b) contain a polymerase, a labeled (e.g., fluorescently-labeled) nucleotide, or a mixture thereof, provided that the solid support is in contact with either of the polymerase and the labeled nucleotide, and wherein the signal on the solid support is generated by the labeled nucleotide of the nucleic acid that complementarily binds to the solid support, and the labeled nucleotide is polymerized to a 3' end of the sequencing primers via the polymerase with the nucleic acid molecule on the solid support as a template. In such an embodiment, the regeneration solution of the step d) contains a reagent for removing the label from the labeled (e.g., fluorescently labeled) nucleotide. In a preferred embodiment of performing sequencing-by-synthesis of a nucleic acid molecule by using the immersion reaction protocol described herein, in the step b), the solid support is immersed in a reaction solution, wherein the reaction solution comprises a polymerase and a labeled (e.g., fluorescently labeled) nucleotide.

The labeled (e.g., fluorescently labeled) nucleotide and the reagent for removing the label from the labeled (e.g., fluorescently labeled) nucleotide suitable for use in the sequencing-by-synthesis are well known in the art, and non-limiting examples of such nucleotide and reagent can be the nucleotides and the reagents for removing labels from labeled nucleotides as found in, for example, WO04018497, WO04018493, U.S. Pat. Nos. 7,427,673 and 7,057,026 (the disclosures of which are incorporated herein by reference in their entirety).

In certain embodiments, the labeled nucleotide may further comprise a 3' blocking group. The 3' blocking group prevents incorporation of other nucleotides when the labeled nucleotide is polymerized into a growing nucleotide chain. Preferably, the 3' blocking group is removed together with the label in the step d). Suitable 3' blocking groups and reagents for removing 3' blocking groups from nucleotides are well known in the art, and non-limiting examples of such 3' blocking groups and reagents can be found in, for example: Greene & Wuts, Protective Groups in Organic Synthesis, John Wiley & Sons. Guillier; Metzker et al. (Nucleic Acids Research, 22 (20): 4259-4267, 1994); WO91/06678, WO2002/029003, WO2014139596, WO2004/018497, and all of which are incorporated herein by reference in their entirety.

In a preferred embodiment, the label itself on the labeled nucleotide can be used as the 3' blocking group. Without being bound by any theory, for example, such label may be of a size or structure sufficient to block the incorporation of other nucleotides into the polynucleotide chain. The blocking may be due to steric hindrance or may be due to a combination of size, charge, and structure. In certain embodiments, the label and the blocking group on the labeled nucleotide can be different, but preferably the label and the blocking group can be removed from the nucleotide by same means. In such a case, the regeneration reagent of the step d) described herein may comprise a reagent that can simultaneously remove the label and the 3' blocking group from the labeled nucleotide. In other embodiments, the step d) described herein may comprise immersing the solid support respectively into a reagent capable of removing the label from the labeled nucleotide and a reagent capable of removing the 3' blocking group from the labeled nucleotide.

As used herein, the term "polymerase" refers to an enzyme for synthesizing a nucleic acid chain or polymer, including DNA polymerases and RNA polymerases. Preferably, the polymerase used herein is a DNA polymerase. One polymerase that can be used is Sequenase™ (an enzyme derived from phage 7 DNA polymerase that is modified to improve its sequencing properties, see Tabor and Richarson, Proc. Nat. Acad. Sci. USA, 84: 4767-4771 (1987), available from, for example, United States Biochemical Corporation, Cleveland, Ohio). Other polymerases that can be used in place of Sequenase™ include, but are not limited to, Klenow fragment of DNA polymerase I, AMV reverse transcriptase, and Taq polymerase. Further descriptions about the polymerases useful in the methods of the invention can also be found in WO05024010 and WO06120433, the entire contents of which are incorporated herein by reference.

The polymerization conditions commonly used are those of these enzymes known in the art. In the case of Sequenase™, the polymerization conditions comprise: at a temperature in the range of about room temperature to about 45° C.; a buffer solution of pH 7 to 8, preferably pH 7.3 to 7.7; an enzyme concentration of about 0.01 unit/µL to about 1 unit/µL, a reaction time of about 1 to about 20 minutes, preferably 1 to 5 minutes. A typical buffer for Sequenase™ consists of: 0.040M Tris HCl (pH 7.5), 0.050M sodium chloride, 0.010M magnesium chloride, 0.010 M dithiothreitol. In the case of Klenow fragment of DNA polymerase I, the typical condition comprises: at a temperatures in the range of about 10° C. to about 45° C., preferably about 15° C. to about 40° C.; a buffer of pH 6.8 to 7.4, preferably pH 7.0 To 7.4; an enzyme concentration of about 0.01 unit/µL to about 1 unit/µL, preferably about 0.02 to about 0.15 unit/µL, and a reaction time of about 1 to about 40 minutes. A typical buffer for the Klenow fragment of DNA polymerase I consists of: 0.05M trihydroxymethyl aminomethane chloride, pH 7.5, 0.05M magnesium chloride, 0.05M sodium chloride, 0.010M dithiothreitol.

It should be understood that these conditions are only exemplary. When using other polymerases, the conditions that are most suitable for them should be used, as it is often desirable to carry out the polymerization reaction as quickly as possible. For this reason, a temperature of 42° C. is usually required for reverse transcriptase; 24° C. for Klenow polymerase; 37° C. for Sequenase™; and 72° C. for Taq polymerase. Furthermore, in order to enhance the reaction, especially in the presence of modified dNTPs, it may be advantageous to use a significant excess (more than stoichiometric amount) of dNTPs or to modify other conditions such as salt concentration.

As used herein, the term "complementary" or "substantially complementary" refers to hybridization or base pairing or duplex formation between nucleotides or nucleic acids. If a nucleotide of a nucleic acid can form a hydrogen bond with a nucleotide of another nucleic acid at a given position, the two nucleic acids are considered to be complementary to each other at that position. Complementary nucleotides are typically A and T (or A and U) or C and G. When optimal alignment and comparement are performed and nucleotide insertions or deletions are appropriately introduced, if at least about 80%, usually at least about 90% to about 95%, even approximately 98% to 100%, of the nucleotides of one strand and the other are paired, these two single-stranded RNA or DNA molecules are considered to be substantially complementary.

As used herein, the term "hybridization" refers to sufficient hydrogen bonding between complementary nucleotides or nucleotide bases, which can be, for example, Watson-Crick, Hoogsteen or reverse Hoogsteen hydrogen bonding, and which allows stable and specific binding between nucleic acid strands. Hybridization capacity is determined according to stringent conditions, including appropriate buffer concentration and temperature, which allows specific hybridization to a target nucleic acid with a fully or partially complementary region. Therefore, not all nucleotides of a nucleic acid need to be complementary. In addition, a nucleic acid strand is "substantially complementary" when it hybridizes to all, a portion, or an overlapping region of a target nucleic acid. Qualitative and quantitative considerations for establishing stringent hybridization conditions for designing the oligonucleotides or primers of the invention are known in the art, see, for example, Ausubel et al., Short Protocols in Molecular Biology (4th ed., John Wiley & Sons 1999); Sambrook et al., Molecular Cloning: A Laboratory Manual (3rd ed., Cold Spring Harbor Laboratory Press 2001): Nucleic Acid Hybridisation: A Practical Approach (B. D. Hames & S. J. Higgins eds., IRL Press 1985).

As used herein, the term "$T_m$" as used herein generally refers to a temperature at which half of double-stranded nucleic acid molecules are dissociated into single strands. The formula for calculating the $T_m$ of a nucleic acid is well known in the art. As mentioned in standard references, when the nucleic acid is in an aqueous solution with a cation concentration of 0.5M or less, the formula $T_m = 81.5 + 16.6$ (log 10 [Na+]) 0.41 (% [G+C])−675/n−1.0 m can be simply used to estimate the value of $T_m$, in which (G+C) content is between 30% and 70%, n is the number of bases, and m is the percentage of mismatched base pairs (see, for example, Sambrook J et al. (2001), Molecular Cloning, A Laboratory Manual, ($3^{rd}$ Ed., Cold Spring Harbor Laboratory Press). Other references disclose more complex calculation methods that take structural and sequence characteristics into account when calculating $T_m$ (see also, Anderson and Young (1985), Quantitative Filter Hybridization, Nucleic Acid Hybridization, and Allawi and Santa Lucia (1997), Biochemistry 36: 10581-94).

Therefore, in a specific embodiment of the present invention, a suitable temperature control device can be used to adjust the temperature in each reaction container to the temperature required for the reaction of the reaction solution or for the washing with the washing solution therein. In one embodiment, the temperature required for each reaction container may be different. In another embodiment, the temperature required for each reaction container may be partially the same. In another embodiment, the temperature required for each reaction container may be the same. For example, the temperatures of the reaction containers respectively containing the one or more reaction solutions in the step b) described herein may be the same or different from each other, and may be the same or different from the temperature of the reaction container in the step d). In one embodiment, one temperature control device can be used to control the temperatures of all reaction containers. In another embodiment, especially when the temperatures required for each of the reaction containers are not the same, different temperature control devices may be used to control the temperatures of the reaction containers separately. Suitable temperature control device that can be used in the method of the present invention is readily available, for example, various commercially available temperature control device, such as water bath. When performing nucleic acid sequencing, the temperature of each reaction container may be dependent on the sequencing method and determined routinely based on the reaction performed in the reaction container, and the temperature of each reaction container may be, for example, but not limited to, at least about 0° C., at least about 5° C., at least about 10° C., at least about 15° C., at least about 20° C., at least about 25° C., at least about 30° C., at least about 35° C., at least about 40° C., at least about 45° C., at least about 50° C., at least about 55° C., at least about 60° C. or higher. In some cases, temperatures below 0° C. may be required.

As used herein, the term "signal" refers to any signal that can be detected, including but not limited to optical signals, electrical signals, electromagnetic signals, radiation signals, and the like. The term "signal representing a nucleotide sequence of a nucleic acid molecule" means that the signal carries information about the nucleotide sequence and can be decoded into the nucleotide sequence of the nucleic acid molecule to be sequenced. For example, in the case where a labeled (e.g., fluorescently labeled) sequencing probe is used, the signal generated by the label carries the nucleotide sequence information of the sequencing probe, and the signal can be used to obtain the nucleotide sequence of the nucleic acid molecule to be sequenced at the position complementary to the sequencing probe. As another example, in the case where a labeled (e.g., fluorescently labeled) nucleotide is used, the signal generated by the label carries the identity information of the nucleotide, and the signal can be used to obtain the nucleotide sequence of the nucleic acid molecule to be sequenced at the position complementary to the nucleotide. In a preferred embodiment, the signal is a fluorescent signal. In a preferred embodiment, the label is a fluorescent label. The methods for detecting the fluorescent label or signal are well known in the art. This can be achieved, for example, by a device that detects the wavelength of fluorescence. Such devices are well known in the art. For example, such a device may be a confocal scanning microscope that scans the surface of a solid support with a laser in order to image a fluorophore that directly binds to a nucleic acid molecule to be sequenced. In addition, each of the generated signals can be observed, for example, with a sensitive 2-D detector, such as a charge-coupled detector (CCD). Other techniques such as scanning near-field optical microscopy (SNOM) can also be used, for example.

In one embodiment, prior to the step c), i.e., prior to detecting the signal on the solid support, the solid support is contacted with a protecting reagent for protecting the nucleic acid molecule, the labeled probe, and/or the labeled nucleotide during detection; for example, the solid support can be immersed in a reaction container containing the protecting reagent. The protecting agent as used herein may be, for example, an agent that prevents dehydration or degradation of nucleic acids, an agent that prevents fluorescence quenching, and the like. Such protecting agents include, but are not limited to, p-phenylenediamine (PPD), propyl gallate (NPG), 1,4-diazobicyclo-octane (DABCO), ascorbic acid (vitamin C), Vectashield, SlowFade, SlowFade Light, etc.

The washing solution as used herein can be any solution that is capable of washing off a substance non-specifically bound to the solid support and does not adversely affect subsequent reactions. Suitably, the washing reagent contains a buffer, such as an organic salt, to maintain a stable pH of about pH 6 to pH 9, and may also contain a monovalent or divalent cation to remove a non-specifically bound molecule from the solid support. Exemplary washing reagents may include, for example, 100 mM Tris-HCl buffer at pH 6.5, TE buffer (Tris-HCl pH 8, 10 mM and EDTA, 1 mM), and the like. According to practical requirements, the washing solution used in each step of the immersion reaction protocol described herein may be the same or different, and may be adaptively adjusted and selected depending on the sequencing method in use, and such adjustments and selections are all within the capabilities of those skilled in the art.

In the methods of the invention, the reagents for sequencing nucleic acid may or may not be reused. For example, the one or more reaction solutions in the step b) and/or the regeneration solution in the step d) can be reused at least once, such as at least 2, 3, 4, 5, 6, 7, 8, 9, 10, 11, 12, 13, 14, 15, 16, 17, 19, 20, 21, 22, 23, 24, 25, 26, 27, 28, 29, 30, 40, 50, 60, 70, 80, 100 or more times. Therefore, in one embodiment of the immersion reaction protocol described herein, the method further comprises, during optionally repeating the steps b) to e) in the step f), the one or more reaction solutions of the step b) and/or the regeneration solution of the step d) may or may not be replaced.

Generally, the number of times of reusing the reaction solutions is related to the weakening degree of the sequencing signal. That is, if the sequencing signal is significantly weakened after the reaction solutions are reused so that the sequencing result is inaccurate, such reuse is inappropriate, and thus, the reaction solutions should be replaced with fresh reaction solutions. In a preferred embodiment, the one or more reaction solutions in the step b) can be reused at least 10 times without significantly affecting the strength of the sequencing signal. In a preferred embodiment, the regeneration solution in the step d) can be reused at least 20 times without significantly affecting the strength of the sequencing signal.

Alternatively, the time for replacing the reaction solution may be determined according to the reaction time between the reaction solution and the solid support during each reaction procedure. The reaction time between the reaction solution and the solid support during each sequencing reaction depends on the reaction to be performed and the reaction temperature. For example, in the case of the sequencing reaction (for example, in the reaction container of the step b)), the reaction temperature may be a temperature suitable for exerting the function of the used sequencing enzyme (such as ligase or polymerase), and for example, may be at least about 5° C., at least about 10° C., at least about 15° C., at least about 20° C., at least about 25° C., at least about 30° C., at least about 35° C., at least about 40° C., at least about 45° C., at least about 50° C., at least about 55° C., at least about 60° C. or higher, such as a temperature in the range of about 10° C. to about 45° C., preferably about 15° C. to about 40° C. Such a temperature can be easily determined by those skilled in the art based on the sequencing enzyme as used. The time of each sequencing reaction may be the time required for the sequencing enzyme as used to incorporate the labeled probe or nucleotide into the template nucleic acid strand, and such time can be easily determined by those skilled in the art, for example, it can be at least 1 s, at least 5 s, at least 10 s, at least 15 s, at least 20 s, at least 25 s, at least 30 s, at least 40 s, at least 50 s, at least 1 minute, at least 1.5 minutes, at least 2 minutes, at least 2.5 minutes, at least 3 minutes, at least 3.5 minutes, at least 4 minutes, at least 5 minutes, at least 10 minutes, at least 15 minutes, at least 20 minutes, at least 30 minutes, or longer. As another example, in the case of the reaction for removing the label from the labeled probe or nucleotide (for example, in the reaction container of the step d)), the reaction temperature may be a temperature suitable for the reaction to be performed, for example, it may be at least about 5° C., at least about 10° C., at least about 15° C., at least about 20° C., at least about 25° C., at least about 30° C., at least about 35° C., at least about 40° C., at least about 45° C., at least about 50° C., at least about 55° C., at least about 60° C., or higher, such temperature can be readily determined by those skilled in the art based on the method or reagent used to remove the label from the labeled probe or nucleotide. The time for such reaction can be easily determined by those skilled in the art, for example, it can be at least 1 s, at least 5 s, at least 10 s, at least 15 s, at least 20 s, at least 25 s, at least 30 s, at least 40 s, at least 50 s, at least 1 minute, at least 1.5 minutes, at least 2 minutes, at least 2.5 minutes, at least 3 minutes, at least 3.5 minutes, at least 4 minutes, at least 5 minutes, at least 10 minutes, at least 15 minutes, at least 20 minutes, at least 30 min or more.

Therefore, in an embodiment where the sequencing reaction in the step b) is performed at a temperature of at least about 5° C., at least about 10° C., at least about 15° C., at least about 20° C., at least about 25° C., at least about 30° C., at least about 35° C., at least about 40° C., at least about 45° C., at least about 50° C., at least about 55° C., at least about 60° C., or higher, the reagents for sequencing reaction may be replaced at a time interval of less than or equal to about 1 hour, less than or equal to about 2 hours, less than or equal to about 3 hours, less than or equal to about 4 hours, less than or equal to about 5 hours, less than or equal to about 6 hours, less than or equal to about 7 hours, less than or equal to about 8 hours, less than or equal to about 9 hours, less than or equal to about 10 hours, less than or equal to about 12 hours, less than or equal to about 15 hours, less than or equal to about 18 hours, less than or equal to about 20 hours, less than or equal to about 22 hours, less than or equal to about 24 or more hours, preferably less than or equal to about 4 hours or 10 hours. In a preferred embodiment, when the reaction temperature of the one or more reaction solutions in the step b) is below about 55° C., the time interval for replacing the one or more reaction solutions in the step b) is less than about 8 hours, preferably about 4 hours. In a preferred embodiment, when the reaction temperature of the one or more reaction solutions in the step b) is below about 45° C., the time interval for replacing the one or more reaction solutions in the step b) is less than about 24 hours, preferably about 10 hours.

Compared with the flow channel reaction protocol adopted by the current second-generation sequencing technology, the immersion reaction protocol of the present invention is at least different in that the method of the present invention allows simultaneously immersing more than one solid support, thereby greatly improving the sequencing throughput. For example, the method of the present invention allows simultaneously immersing 2, 3, 4, 5, 6, 7, 8, 9, 10, 11, 12, 13, 14, 15, 16, 17, 18, 19, 20 or more solid supports. Such more than one solid support that are simultaneously immersed is referred to herein as a batch of solid supports. However, it should be understood that such a batch of solid supports may also consist of only one solid support.

More specifically, the immersion reaction protocol of the present invention enables a nested batch processing of solid supports. The nested batch processing comprises, during a process of performing a nucleic acid sequencing on a first batch of solid supports using the immersion protocol of the present invention, the nucleic acid sequencing on another batch of solid supports (i.e., a second batch of solid supports) starts before the first sequencing cycle is completed, and after the nucleic acid sequencing on the second batch of solid supports begins, the nucleic acid sequencing on a third batch of solid supports may start as well; similarly, after the nucleic acid sequencing on an $(N-1)^{th}$ batch of solid supports starts, the nucleic acid sequencing on an N batch of solid supports may start, provided that $1 \leq N \leq t_{cycle}/t_{speed-limit}$, wherein N is an integer value, $t_{cycle}$ is the total time from the step b) to the step e) (it is referred to herein as the total time of a sequencing cycle, so that each "sequencing cycle" as used herein begins at immersing solid supports into one or more reaction solutions of the step b) and ends at washing the solid supports in the step e) in the immersion reaction protocol of the present invention), $t_{speed-limit}$ is the time of the longest procedure in each immersing and washing in the step b), detecting in the step c), immersing in the step d), and washing in the step e) (hereinafter referred to as the time of speed-limiting procedure). Therefore, for example, if the total time of a sequencing cycle is 120 seconds, and the speed-limiting procedure in the sequencing cycle is the detecting procedure of the step c), which requires 40 seconds, then based on the above equation, N≤120 s/40 s=3, so that at most N=3 batches of solid supports can be performed in nested batch processing manner in a single sequencing cycle. As another example, if the total time of a sequencing cycle is 120 seconds, and the speed-limiting procedure in the sequencing cycle is the detection procedure of the step c), which requires 35 seconds, then based on the above equation, N≤120 s/35 s=3.4, so that at most N=3 batches of solid supports can be performed in nested batch processing manner in a single sequencing cycle. In the embodiment of the present invention, at most N=1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more batches of solid supports can be performed in nested batch processing manner in a single sequencing cycle. In a preferred embodiment, the time of other procedures in a sequencing cycle can be adjusted based on the time required by the speed-limiting procedure so that the total time of the sequencing cycle is exactly an integral multiple of the time required by the speed-limiting procedure.

Therefore, in one embodiment, the immersion reaction protocol as described herein further comprises: after immersing a first batch of solid supports in one or more reaction solutions of the step b) and before the end of the step e), immersing a second batch of solid supports having nucleic acid molecules immobilized thereon in the one or more reaction solutions of the step b), and then operating the second batch of solid supports according to the steps b) to f); optionally iteratively repeating this process for N−1 times, wherein $1 \leq N \leq t_{cycle}/t_{speed-limit}$, wherein N is an integer value, $t_{cycle}$ is the total time from the step b) to the step e), and $t_{speed-limit}$ is the time of the longest procedure in each immersing and washing in the step b), detecting in the step c), immersing in the step d), and washing in the step e). As used herein, "iteratively repeating" means that after immersing a first batch of solid supports in the one or more reaction solutions of the step b) and before the end of the step e), optionally a second batch of solid supports having nucleic acid molecules immobilized thereon is immersed in the one or more reaction solutions of the step b), and then after the second batch of solid supports is immersed in the one or more reaction solutions of the step b) and before the end of the step e), optionally a third batch of solid supports having nucleic acid molecules immobilized thereon is immersed in the one or more reaction solutions of the step b), and then after the third batch of solid supports is immersed in the one or more reaction solutions in the step b) and before the end of the step e), optionally a fourth batch of solid supports having nucleic acid molecules immobilized thereon is immersed in the one or more reaction solutions in the step b), and so on, until the $(N+1)^{th}$ batch of solid supports is iteratively and repeatedly subjected to this process, where $1 \leq N \leq t_{cycle}/t_{speed-limit}$, and N is an integer value.

In practice, the time interval between immersing an $N^{th}$ batch of solid supports in the one or more reaction solutions of the step b) and immersing a $(N+1)^{th}$ batch of solid supports in the one or more reaction solutions of the step b) meets the following conditions:

$$t_N \geq t_{speed-limit}, \text{ and } \sum_{N=1}^{N} t_N \leq t_{cycle} - t_{speed-limit}.$$

In one embodiment, the method of the present invention allows N=1, 2, 3, 4, 5, 6, 7, 8, 9, 10, 11, 12, 13, 14, 15, 16, 17, 17, 18, 19, 20, 21, 22, 23, 24, 25, 26, 27, 28, 29, 30 or more batches of solid supports to be used in one sequencing cycle. Therefore, compared with the existing second-generation sequencing technology, the immersion reaction protocol of the present invention greatly improves the sequencing throughput and is capable of sequencing more nucleic acids in a unit time.

In one embodiment, the immersion reaction protocol provided by the present invention further comprises: adding an appropriate amount of a humectant to the one or more reaction solutions in the step b), the regeneration solution in the step d) and/or the washing solution in the step e). In a preferred embodiment, an appropriate amount of a humectant is added to a first reaction solution. Without being bound by any theory, it is believed that the addition of such a humectant may help to avoid the drying of surface of solid supports that may be caused by evaporation and hydrophobicity when the solid supports are removed from the reaction solution and/or washing solution to expose to air. Such humectants include, but are not limited to, polyhydric alcohols such as glycerol, propylene glycol, 1,3-butanediol, sorbitol, polyethylene glycol, and the like. It should be understood that the addition of such a humectant should not cause any adverse effect on the reaction solution and/or the washing solution, the solid supports, and the nucleic acid molecules on the solid supports, and it should not cause a significant increase of the amount of reagents carried on the solid supports. In a preferred embodiment, an appropriate amount of glycerol is added to the one or more reaction solutions of the step b), the regeneration solution in the step d) and/or the washing solution in the step e). The amount of the added humectant may be any effective amount capable of keeping the surface of the solid support moist. It should be understood that such an amount should not cause any adverse effects on the reaction solution and/or the washing solution, the solid support, and the nucleic acid molecules on the solid supports, and it should not cause a significant increase in the amount of reagents carried on the solid supports. The amount of the added humectant may be, for example, based on the volume of the reaction solution and/or the washing solution, an amount of at least about 0.05%, at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20% or more. In a preferred embodiment, about 5% to 10% glycerol (v/v) is added to the one or more reaction solutions in the step b), the regeneration solution in the step d) and/or the washing solution in the step e).

In one embodiment, the immersion reaction protocol provided by the present invention further comprises: adding into the one or more reaction solutions in the step b), the regeneration solution and/or the washing solution in the step d) an appropriate amount of a reagent for retaining the reaction solution and/or the washing solution remaining on the solid support thereon when the solid support is taken out from the reaction solution and/or the washing solution. Without being bound by any theory, it is believed that the addition of such reagent may help to avoid the drying caused by the separation of the reaction solution and/or the washing solution remaining on the solid support from the upper end of the solid support due to the gravity when the solid support is taken out from the reaction solution and/or the washing solution. As used herein, the upper end of the solid support refers to an end that is firstly exposed to air when the solid support is taken out from the solution. In a preferred embodiment, such an reagent may be, for example, a surfactant. Such surfactant may include, but is not limited to, polysorbate 20, stearic acid, lauric acid, sodium lauryl sulfate, sodium dioctyl succinate sulfonate (Aerosol-OT), sodium dodecylbenzenesulfonate, sodium glycocholate, benzalkonium chloride, benzalkonium bromide, lecithin, fatty glycerides and the like. It should be understood that the addition of such reagent, such as a surfactant, should not cause any adverse effects on the reaction solution and/or the washing solution, the solid supports, and the nucleic acid molecules carried on the solid supports, and should not cause a significant increase in the amount of reagents carried on the solid supports. In a preferred embodiment, an appropriate amount of polysorbate 20 is added to the one or more reaction solutions of the step b), the regeneration solution and/or the washing solution of the step d). Such a reagent, for example, a surfactant, may be added in any effective amount capable of retaining the reaction solution and/or the washing solution remaining on the solid support thereon when the solid support is taken out from the reaction solution and/or the washing solution. It should be understood that such an amount should not cause any adverse effects on the reaction solution and/or the washing solution, the solid supports, and the nucleic acid molecules carried on the solid supports, and it should not cause any significant increase in the amount of reagents carried on the solid supports. The amount of such added reagent, such as a surfactant, can be, for example, at least about 0.001%, at least about 0.005%, at least about 0.01%, at least about 0.02%, at least about 0.03%, at least about 0.04%, at least about 0.05%, at least about 0.06%, at least about 0.07%, at least about 0.08%, at least about 0.09%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 2%, at least about 3%, at least about 4%, at least about 5%, or more, based on the volume of the reaction solution and/or the washing solution. In a preferred embodiment, about 0.05% to 1% of polysorbate 20 (v/v) is added to the one or more reaction solutions of the step b), the regeneration solution and/or the washing solution of the step d).

In one embodiment, the immersion reaction protocol provided by the present invention further comprises: optimizing a motion speed of the solid support between the reaction containers, so as to minimize the time that the solid support is exposed to the air. It should be understood that such optimization of the motion speed should not cause any adverse effects on the reaction solution, the solid support, and the nucleic acid molecules carried on the solid support.

Therefore, in a specific embodiment, optimizing the motion speed of the solid support between the reaction containers comprises optimizing the speed at which the solid support is taken out from the solution or reagent in the reaction container so that the solid support is taken out from the solution or reagent as quickly as possible without causing any adverse effects on the reaction solution, the solid support, and the nucleic acid molecules carried on the solid support due to the faster removal. Without being bound by any theory, it is believed that the faster removal of the solid support from the solution or reagent can help to avoid the drying of the surface thereof due to evaporation and hydrophobicity, and can also help to reduce the amount of solution or reagent carried on the surface thereof, thereby reducing the contamination to subsequent procedures. However, too fast removal speed may cause damage to the solid support and nucleic acid molecules immobilized thereon, and affect the sequencing quality. Therefore, the removal speed may be optimized depending on the specific solid support as used, the nucleic acid molecules immobilized thereon and the reaction solution or reagent. In one embodiment, the speed at which the solid support is removed from the solution or reagent in the reaction container may be, for example, but not limited to, at least 1 mm/s, at least 5 mm/s, at least 10 mm/s, at least 15 mm/s, at least 20 mm/s, at least 25 mm/s, at least 30 mm/s, at least 40 mm/s, at least 50 mm/s or more. In another embodiment, the speed at which the solid support is removed from the solution or reagent in the reaction container may be, for example, but not limited to, not higher than 50 mm/s, not higher than 40 mm/s, not higher than 30 mm/s, not higher than 20 mm/s, not higher than 10 mm/s, or lower. In a preferred embodiment, the speed at which the solid support is removed from the solution or reagent in the reaction container may be, for example, about 20 mm/s.

In a specific embodiment, optimizing the motion speed of the solid support between the reaction containers comprises optimizing the motion speed of the solid support after being taken out from the solution or reagent in the reaction container, so as to minimize the time that the solid support is exposed to air. Without being bound by any theory, it is believed that moving the solid support as quickly as possible after removing it from the solution or reagent in the reaction container helps to avoid the drying of the surface thereof which may be caused by evaporation and hydrophobicity. In one embodiment, the motion speed of the solid support after being removed from the solution or reagent in the reaction container is optimized so that the solid support is exposed to air for a time of less than or equal to 100 ms, less than or equal to 200 ms, less than or equal to 500 ms, less than or equal to 1 s, less than or equal to 1.5 s, less than or equal to 2 s, less than or equal to 2.5 s, less than or equal to 3 s, less than or equal to 3.5 s, less than or equal to 4 s, less than or equal to 4.5 s, less than or equal to 5 s, less than or equal to 5.5 s, less than or equal to 6 s, less than or equal to 6.5 s, less than or equal to 7 s, less than or equal to 7.5 s, less than or equal to 8 s, less than or equal to 8.5 s, less than or equal to 9 s, less than or equal to 9.5 s, less than or equal to 10 s, less than or equal to 15 s, less than or equal to 20 s, less than or equal to 30 s, less than or equal to 1 min, less than or equal to 2 min, less than or equal to 5 min or less than or equal to 10 min.

Therefore, in a preferred embodiment, the present invention provides a method for sequencing a nucleic acid using an immersion reaction protocol, wherein the immersion reaction protocol comprises the following steps:

a) providing a first batch of solid supports having nucleic acid molecules immobilized thereon, b) immersing the first batch of solid supports in one or more reaction solutions to generate a signal representing a nucleotide sequence of the nucleic acid molecule on the solid support, wherein each of the one or more reaction solutions is placed in a separate reaction container, wherein, after removing the first batch of solid supports from each of the reaction solution, washing the first batch of solid supports to remove the reaction solution remaining on the solid support, c) detecting the signal on the first batch of solid supports, d) immersing the first batch of solid supports in a regeneration solution placed in another reaction container to eliminate the signal on the solid support, e) removing the first batch of solid supports from the regeneration solution, and washing the first batch of solid supports to remove the regeneration solution remaining on the solid supports, and f) optionally, repeating the steps b) to e) or the steps b) to c), wherein a humectant such as glycerol, and/or a surfactant such as polysorbate 20 are optionally added to the one or more reaction solutions of the step b), the regeneration solution and/or the washing solution of the step d), and optionally the motion speed of the solid support between the reaction containers is optimized to minimize the time that the solid support is exposed to air, optionally, the method further comprises that the $2^{nd}$ to $N^{th}$ batches of solid supports are iteratively and repeatedly subjected to the procedures as described herein (i.e., nested batch processing), wherein $1 \leq N \leq t_{cycle}/t_{speed-limit}$, and N is an integer value.

In another preferred embodiment, the present invention provides a method for sequencing-by-ligation of a nucleic acid using an immersion reaction protocol, wherein the immersion reaction protocol comprises the following steps:

a) providing a first batch of solid supports having nucleic acid molecules immobilized thereon, b) immersing the first batch of solid supports in a reaction solution (referred to herein as a first reaction solution) placed in a reaction container, wherein the first reaction solution comprises a ligase and a labeled (e.g., fluorescently labeled) sequencing probe, optionally further comprises an anchor probe, wherein a nucleic acid ligation reaction is performed between the anchor probe and the sequencing probe in the reaction container using the nucleic acid molecule as a template, and removing the first batch of solid supports from the first reaction solution, and washing the first batch of solid supports to remove the first reaction solution remaining on the solid supports, c) detecting the label on the first batch of solid supports, d) immersing the first batch of solid supports in a regeneration solution placed in a separate reaction container, wherein the regeneration solution contains a reagent that can remove a label from the labeled (e.g., fluorescently labeled) sequencing probe or a reagent that can remove the labeled (e.g., fluorescently labeled) sequencing probe from the nucleic acid molecule, e) removing the first batch of solid supports from the regeneration solution, and washing the first batch of solid supports to remove the regeneration solution remaining on the solid supports, f) optionally, repeating the steps b) to e) or the steps b) to c), wherein a humectant such as glycerol and/or a surfactant such as polysorbate 20 are optionally added to the first reaction solution, the regeneration solution and/or the washing solution, and optionally the motion speed of the solid support between the reaction containers is optimized so as to minimize the time that the solid support is exposed to air, optionally, the method further comprises that the $2^{nd}$ to $N^{th}$ batches of solid supports are iteratively and repeatedly subjected to the procedures as described herein (i.e., nested batch processing), wherein $1 \leq N \leq t_{cycle}/t_{speed-limit}$, and N is an integer value.

In another preferred embodiment, the present invention provides a method for sequencing-by-synthesis of a nucleic acid using an immersion reaction protocol, wherein the immersion reaction protocol comprises the following steps:

a) providing a first batch of solid supports having nucleic acid molecules immobilized thereon, b) immersing the first batch of solid supports in a reaction solution (referred to herein as a first reaction solution) placed in a reaction container, wherein the first reaction solution comprises a polymerase and a labeled (such as fluorescently labeled) nucleotide, optionally the labeled nucleotide may further comprise a 3' blocking group, wherein the nucleic acid polymerization reaction is performed in the reaction container using the nucleic acid molecule as a template, and removing the first batch of solid supports from the first reaction solution, and washing the first batch of solid supports to remove the first reaction solution remaining on the solid supports, c) detecting the label on the first batch of solid supports, d) immersing the first batch of solid supports in a regeneration solution placed in another reaction container, wherein the regeneration solution contains a reagent that can remove a label from the labeled (e.g., fluorescently labeled) nucleotide, e) removing the first batch of solid supports from the regeneration solution, and washing the first batch of solid supports to remove the regeneration solution remaining on the solid support, f) optionally, repeating the steps b) to e) or the steps b) to c), wherein a humectant such as glycerol and/or a surfactant such as polysorbate 20 are optionally added to the first reaction solution, the regeneration solution and/or the washing solution, and optionally the motion speed of the solid support between the reaction containers is optimized so as to minimize the time that the solid support is exposed to air, optionally, the method further comprises that the $2^{nd}$ to $N^{th}$ batches of solid supports are iteratively and repeatedly subjected to the procedures as described herein (i.e., nested batch processing), wherein $1 \leq N \leq t_{cycle}/t_{speed-limit}$, and N is an integer value.

In other embodiments, the present invention also provides an apparatus for sequencing a nucleic acid molecule using the immersion reaction protocol described herein, the apparatus comprising:

a) one or more reaction containers, each of which contains a reaction solution for contacting nucleic acid molecule to generate a signal representing a nucleotide sequence of the nucleic acid molecule;

b) one or more reaction containers containing a washing reagent;

c) a reaction container containing a reaction solution for eliminating the signal from solid supports;

d) a means for detecting the signal; and e) a temperature control device (such as a water bath) for controlling a temperature of the reaction container(s) in above a) to c).

The embodiments of the present invention will be described in detail below with reference to the drawings and examples. However, those skilled in the art will understand that the following drawings and examples are only used to illustrate the present invention, rather than limiting the scope of the present invention. Various objects and advantageous aspects of the present invention will become apparent to those skilled in the art from the accompanying drawings and the following detailed description of the preferred embodiments.

EXAMPLES

The embodiments of the present invention will be described in detail below with reference to examples, but those skilled in the art will understand that the following examples are only used to illustrate the present invention, and should not be considered as limiting the scope of the present invention. If the specific conditions are not indicated in the examples, the conventional conditions or the conditions recommended by the manufacturer are used. If the reagents or instruments used are not specified by the manufacturer, they are all conventional products that are commercially available.

Example 1: Nucleic Acid Sequencing with Immersion Reaction Protocol

Figure 1:
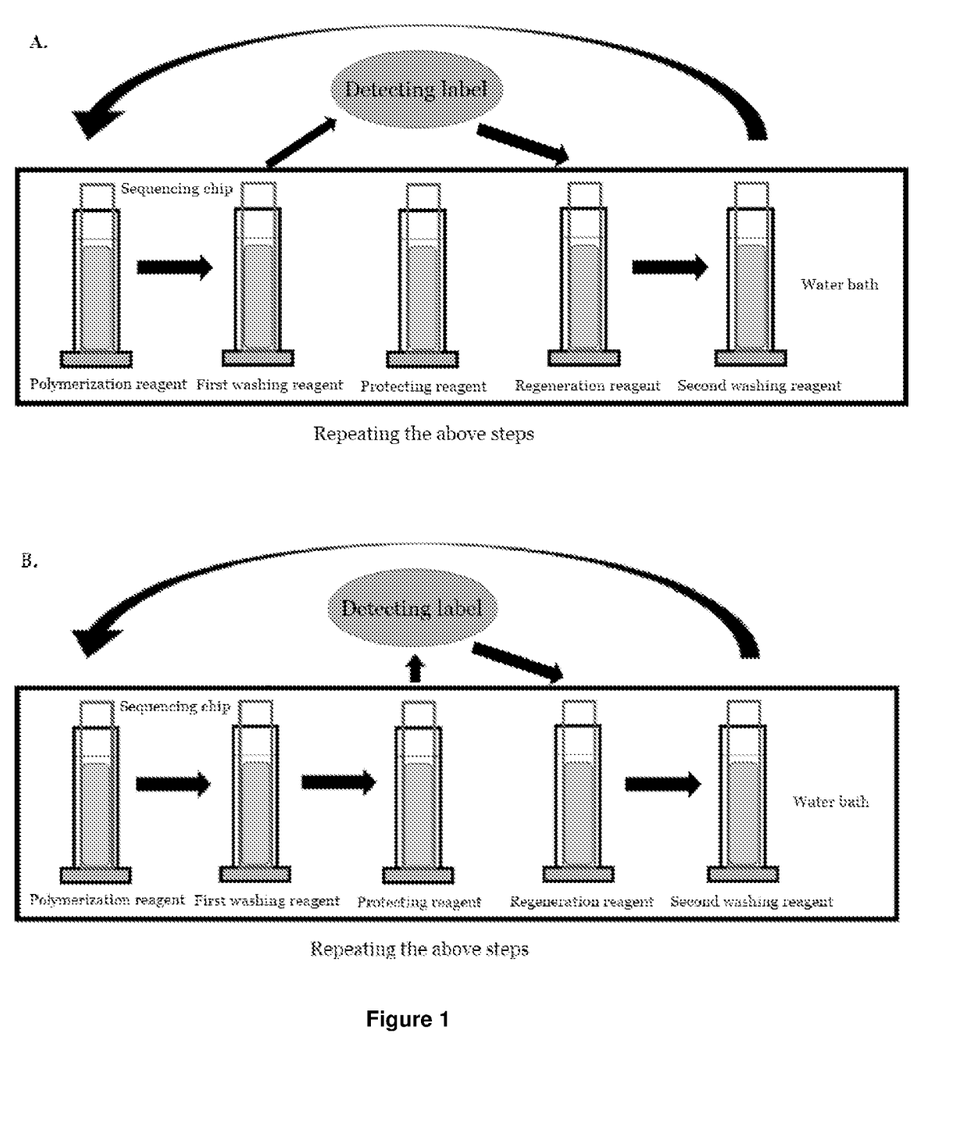
FIG. 1 shows a flowchart (showing a sequencing cycle) of two exemplary embodiments of the immersion reaction protocol of the present invention, one of which uses a protecting reagent that protects the nucleic acid and label during the detection.

According to the manufacturer's instructions, a MGIeasy™ DNA library preparation kit (Shenzhen Huada Zhizao Technology Co., Ltd.) was used to extract DNA from an *E. coli* standard strain as raw materials to prepare a library for sequencing, which was loaded on a sequencing chip. According to the manufacturer's instructions, the reagents in BGISEQ-500 high-throughput kit (SE50 V3.0, Shenzhen Huada Zhizao Technology Co., Ltd., article number: PF-UM-PEV30) were used, and the flowchart in FIG. 1A (an exemplary embodiment of the immersion reaction protocol described herein) was followed to perform 10 cycles of sequencing of the nucleic acid molecule on the obtained chip, in which 3 chips were simultaneously immersed.

Figure 2:
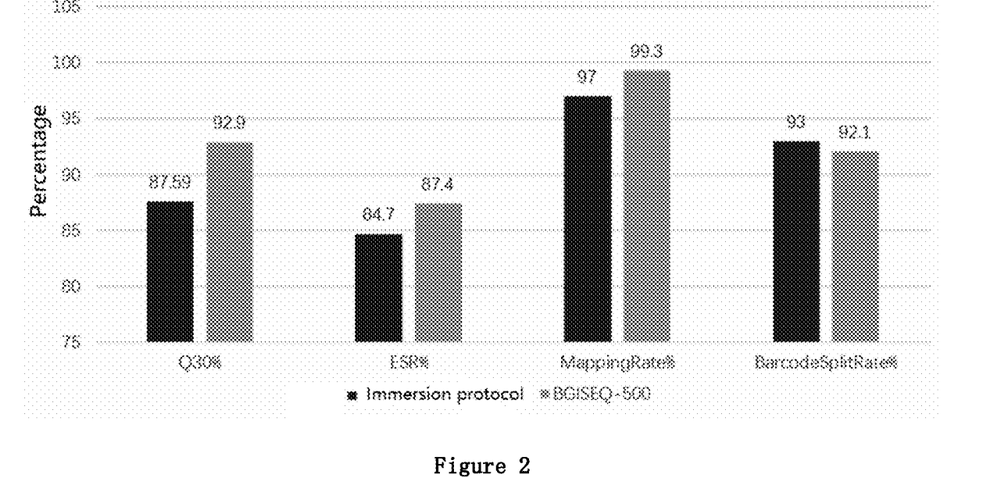
FIG. 2 shows a comparison of sequencing data between the immersion reaction protocol of the present invention and BGISEQ-500 SE50.

The obtained sequencing data were uploaded to BGI Online (see www.bgionline.cn/) for analysis, or the software of the BGISEQ-500 sequencer was used to analyze the quality of the sequencing data and a visual report was output, as shown in FIG. 2.

The MGIEasy™ DNA library preparation kit was used to extract DNA from an *E. coli* standard strain as raw materials to prepare a library for sequencing, which was loaded on a sequencing chip, and the sequencing reagents in the BGISEQ-500 high-throughput kit (SE50 V3.0) were used, to perform a sequencing reaction as control on a BGISEQ-500 sequencer.

In FIG. 2, Q30 referred to the occurrence of one error in 1000 bases as sequenced, in which the larger the number was, the better the sequencing quality was; ESR was a sequencing indicator of the BGISEQ-500 sequencer and referred to the effective DNA nanosphere ratio, in which the larger the number was, the better the sequencing quality was; MappingRate referred to the comparison rate of the sequencing data relative to the reference genome, in which the larger the number was, the better the sequencing quality was; BarcodeSplitRate referred to the barcode split rate, in which the larger the number was, the better the sequencing quality was.

As compared with the control group of using the BGISEQ-500 sequencer to sequence the same chip, the quality of the sequencing data obtained by the immersion reaction protocol of the present invention was basically similar to the quality of those obtained by the BGISEQ-500 sequencer (the difference was within 5%, and the BarcodeSplitRate was better than that of the BGISEQ-500 sequencer).

Example 2: Comparison of Different Immersion Reaction Protocols

Using an experimental procedure similar to Example 1, the chip was subjected to 15 sequencing cycles using different immersion reaction protocols.

Firstly, the chip was sequenced using the following immersion protocol:

Immersion protocol 1: the same experimental procedure as in Example 1 was performed on the chip for 15 sequencing cycles;

Immersion protocol 2: on the basis of Immersion protocol 1, 5-10% glycerol (v/v) was added to the polymerization reaction reagent and the chip was quickly moved at a speed of 20 mm/s during the experiment;

As a control, the chip was sequenced using a BGISEQ-500 sequencer.

The decrease rate of the fluorescence signal intensity detected in the 15th sequencing cycle relative to the fluorescence signal intensity detected in the 5th sequencing cycle was calculated For these three kinds of sequencing procedures, respectively. The results were shown in FIG. 3, where A represented the fluorescence signal for detecting base A; C represented the fluorescence signal for detecting base C; G represented the fluorescence signal for detecting base G; T represented the fluorescence signal for detecting base T; AVG represented the average value of the fluorescence signals for detecting the four bases.

Figure 3:
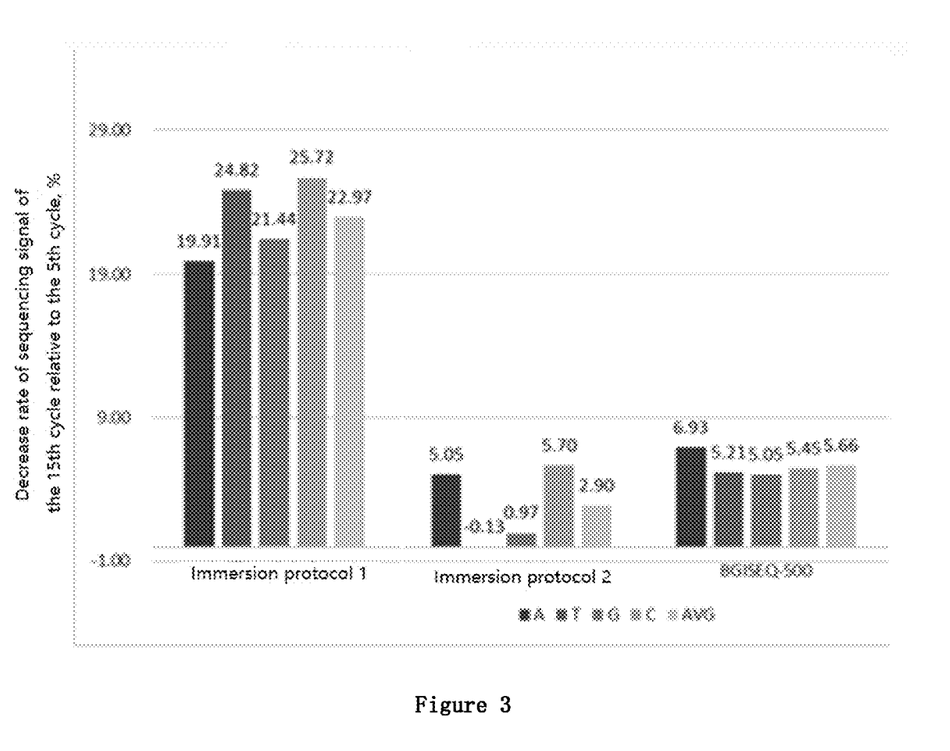
FIG. 3 shows sequencing results of the improved immersion reaction protocol of the present invention.

We found that after adding glycerol and increasing the chip lifting speed to 20 mm/s, the decrease rate of the fluorescence signal of the 15th cycle relative to that of the 5th cycle dropped to about 10%, which showed a noticeable improvement in comparison with the decrease rate of more than 20% for the Immersion protocol 1 (see FIG. 3).

Figure 4:
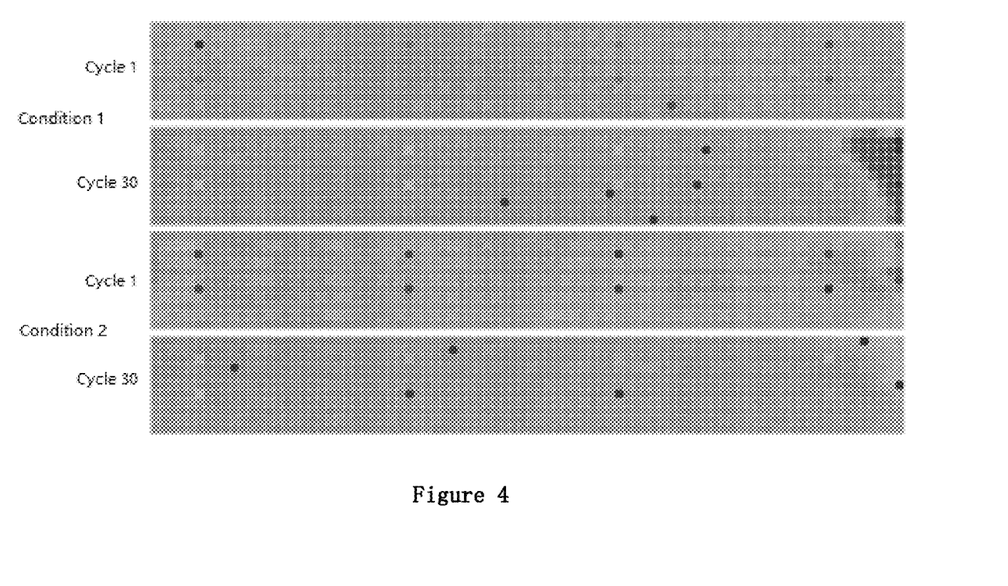
FIG. 4 shows the improvement of the drying of the upper end of the chip by adding a certain amount of surfactant to the polymerization reagent. The left side of the figure shows the lower end of the chip, and the right side of the figure shows the upper end of the chip. Condition 1: adding 5% to 10% glycerol (v/v) in the first reaction solution+quickly moving chip; Condition 2: adding 10% glycerol (v/v) in the first reaction solution+quickly moving chip+adding 0.05% to 1% polysorbate 20 (v/v) in the first reaction solution.

In addition, based on 5% to 10% glycerol (v/v)+quickly moving chip (Condition 1), 0.05% to 1% polysorbate 20 (v/v, Condition 2) was further added to the sequencing reagent. Using the same experimental procedure as in Example 1, after performing a plurality of sequencing cycles on the chip, the analysis software of the BGISEQ-500 sequencer was used to obtain a heat map of the sequencing signal values on the chip. The results were shown in FIG. 4. It was found that compared with the chip sequenced under Condition 1, the drying phenomenon at the upper end of the chip sequenced under Condition 2 was significantly alleviated, and the data qualities at the upper end of the chip and the other regions of the chip were not significantly different (if the surfactant was not added, the signal value at the upper end of the chip decreased significantly after 30 cycles; while after a certain amount of polysorbate 20 was added, the signal value at the upper end of the chip was not significantly different from those at other regions, which indicated the uniformity was better) (as shown in FIG. 4).

Example 3: Nested Batch Processing of the Immersion Reaction Protocol of the Present Invention According to an embodiment of the immersion reaction protocol of the present invention, a nested batch processing of chips was applied in the experimental procedure of Example 1. When the fluorescence labeling detection was performed after the polymerization reaction of the three chips of the first group was completed, the other three chips of the second group were immersed in a sequencing reaction reagent (i.e., a first reaction solution) to start the sequencing reaction. In the experiment, the polymerization reagent was replaced every 10 sequencing cycles, and the regeneration reagent was replaced every 20 sequencing cycles. By comparison, the cost was 25% of the same kind of sequencing of BGISEQ-500 sequencer. Finally, a total of 60 complete sequencing cycles for all of the two groups of chips were completed in 2 hours. In contrast, on the current BGISEQ-500 sequencer or illumina HiSeq-2500 platform, it took more than 10 hours to finish 60 complete sequencing cycles. Therefore, in the same sequencing time, the sequencing throughput of the present invention was more than five times that of the BGISEQ-500 sequencer or HiSeq-2500 platform, and the throughput could be further increased and the cost could be further reduced by increasing the number of batches for the nested batch processing.

Example 4: Reuse of Sequencing Reagents Did not Affect Sequencing Quality

The sequencing reagents that had been used in Example 1 were again used to perform the sequencing procedure described in Example 1, and the sequencing data were analyzed as described in Example 1 and compared with the unused reagents. The comparison results were shown in Table 1 below, showing that the used reagents could perform sequencing normally.

TABLE 1

Comparison of the used and unused reagents:

| Conditions | Sequencing reagents after 60 sequencing cycles | Unused sequencing reagents |
|---|---|---|
| Number of cycles | 50 | 50 |
| Total reads number (M) | 185.14 | 185.98 |
| Reads number on alignment (M) | 184.17 | 184.75 |
| Q30% | 92.17 | 91.35 |
| Effective reads rate, % | 84.39 | 84.33 |
| Comparison rate, % | 99.47 | 99.34 |
| Sequencing error rate, % | 0.1 | 0.17 |

Example 5: Study on the Stability of Reagents Used in the Immersion Reaction Protocol of the Present Invention The sequencing reagents (the sequencing reagents referred to Example 1, including polymerization reagent, washing reagent 1, washing reagent 2, and regeneration reagent) were separately placed in 45° C. and 55° C. water baths and processed for different times, including 4 hours, 8 hours, and 24 hours.

The heat-treated reagents were then used to perform nucleic acid sequencing on a BGISEQ-500 sequencer, and the qualities of the sequencing data were compared by using the software provided by the BGISEQ-500 sequencer to determine the reagent stability.

The analysis results of the sequencing data qualities were shown in Table 2. It could be seen that the sequencing reagents were still stable after being treated at 55° C. for 4 hours or at 45° C. for 8 hours, and the sequencing qualities were essentially similar to that of the control group of using the reagents that were not subjected to the heat treatment. Therefore, based on this result, the replacement cycle of the sequencing reagents in the immersion reaction protocol could be determined to be 4 hours at 55° C., or 10 hours at 45° C.

TABLE 2

Stability analysis of sequencing reagents in immersion reaction protocol: Sequencing reagents heat-treated at 45° C.

|  | Q30% | ESR % | Mapping Rate % | Sequencing error rate, % |
|---|---|---|---|---|
| Control | 92 | 78.6 | 98.4 | 0.41 |
| Heat-treatment, 4 h | 89.2 | 78 | 90.2 | 0.59 |
| Heat-treatment, 8 h | 90.1 | 92.3 | 98.3 | 0.43 |
| Heat-treatment, 24 h | 85.5 | 80.1 | 96.8 | 0.68 |

Sequencing reagents heat-treated at 55° C.

|  | Q30% | ESR % | Mapping Rate % | Sequencing error rate, % |
|---|---|---|---|---|
| Control | 92.2 | 78.4 | 97.8 | 0.41 |
| Heat-treatment, 4 h | 92.1 | 79.6 | 95.2 | 0.39 |
| Heat-treatment, 8 h | 89.8 | 77.5 | 91.5 | 0.66 |
| Heat-treatment, 24 h | 79.7 | 79.2 | 79.3 | 1.39 |

What is claimed is:

1. A method for sequencing a nucleic acid using an immersion reaction protocol, the immersion reaction protocol comprising the following steps:
    a) providing a first batch of solid supports having nucleic acid molecules immobilized thereon,
    b) immersing the first batch of solid supports in one or more reaction solutions to generate a signal representing a nucleotide of the nucleic acid molecule on the solid supports, wherein each of the one or more reaction solutions is placed in a separate reaction container, wherein, after removing the first batch of solid supports from each of the reaction solutions, washing the first batch of solid supports to remove the reaction solution remaining on the solid supports,
    c) detecting the signal on the first batch of solid supports,
    d) immersing the first batch of solid supports in a regeneration solution placed in another reaction container to eliminate the signal on the solid supports,
    e) removing the first batch of solid supports from the regeneration solution, and washing the first batch of solid supports to remove the regeneration solution remaining on the solid supports, and
    f) optionally, repeating the steps b) to e) or the steps b) to c), and
    g) determining the nucleotide sequence of the nucleic acid molecule based on the detected signals.

2. The method according to claim 1, which further comprises: after immersing the first batch of solid supports in the one or more reaction solutions of the step b) and before the end of the step e), immersing a second batch of solid supports having nucleic acid molecules immobilized thereon in the one or more reaction solutions of the step b), and then operating the second batch of solid supports according to the steps b) to f);
    optionally iteratively repeating this process for N−1 times,
    wherein, $1 \leq N \leq t_{cycle}/t_{speed-limit}$, and N is an integer value, wherein, $t_{cycle}$ is a total time from the step b) to the step e), and $t_{speed-limit}$ is the time of the longest procedure in each immersing and washing in the step b), detecting in the step c), immersing in the step d), and washing in the step e).

3. The method according to claim 2, wherein the time interval, $t_N$, between immersing a $N^{th}$ batch of solid supports in the one or more reaction solutions of the step b) and immersing a $(N+1)^{th}$ batch of solid supports in the one or more reaction solutions of the step b) meets the following conditions:

$$t_N \geq t_{speed-limit}, \text{ and } \sum_{N=1}^{N} t_N \leq t_{cycle} - t_{speed-limit}.$$

4. The method according to claim 1, wherein each batch of solid supports consists of one or more solid supports.

5. The method according to claim 1, wherein the signal comprises a fluorescence signal.

6. The method according to claim 1, wherein the sequencing comprises sequencing-by-ligation, sequencing-by-synthesis or sequencing by combinatorial probe-anchor synthesis (cPAS).

7. The method according to claim 6, wherein the sequencing is sequencing-by-ligation, and wherein the one or more reaction solutions of the step b) comprise a solution containing an anchor probe, a labeled sequencing probe, a ligase, or a mixture thereof, provided that the solid support is in contact with each of the anchor probe, the labeled sequencing probe and the ligase, and wherein the signal on the solid support is generated by the labeled sequencing probe that complementarily binds to the nucleic acid molecule on the solid support, the labeled sequencing probe is linked via the ligase to the anchor probe that complementarily binds to the same nucleic acid molecule,
    optionally, the regeneration solution of the step d) comprises a reagent that is capable of removing a label from the labeled sequencing probe or a reagent that is capable of removing the labeled sequencing probe from the nucleic acid molecule.

8. The method according to claim 6, wherein the sequencing is sequencing-by-ligation, further comprising: before the step b), contacting the solid supports having the nucleic acid molecules immobilized thereon with the anchor probe, so that the anchor probe hybridizes to the nucleic acid molecule on the solid supports.

9. The method according to claim 8, wherein the one or more reaction solutions of the step b) comprise a solution containing the labeled sequencing probe, the ligase, or a mixture thereof, provided that the solid support is in contact with each of the labeled sequencing probe and the ligase, and wherein the signal on the solid support is generated by the labeled sequencing probe that complementarily binds to the nucleic acid molecules on the solid support, the labeled sequencing probe is linked via the ligase to the anchor probe that complementarily binds to the same nucleic acid molecule,
    optionally, the regeneration solution of the step d) comprises a reagent that is capable of removing a label from the labeled sequencing probe or a reagent that is capable of removing the labeled sequencing probe from the nucleic acid molecule.

10. The method according to claim 6, wherein the sequencing is sequencing-by-synthesis, and wherein the one or more reaction solutions of the step b) comprise a solution containing a polymerase, sequencing primers, a labeled nucleotide, or a mixture thereof, provided that the solid support is in contact with each of the polymerase, the sequencing primers, and the labeled nucleotide, and wherein the signal on the solid supports is generated by the labeled nucleotides that complementarily bind to the nucleic acid molecules on the solid support, the labeled nucleotide is polymerized to a 3' end of the sequencing primers via the polymerase using the nucleic acid molecule on the solid support as a template, optionally, the regeneration solution of the step d) contains a reagent capable of removing a label from the labeled nucleotide, optionally, the labeled nucleotide further comprises a 3' blocking group.

11. The method according to claim 6, wherein the sequencing is sequencing-by-synthesis, and wherein the nucleic acid molecule is immobilized on the solid support by hybridization of the sequencing primers immobilized on the solid support.

12. The method according to claim 6, wherein the sequencing is sequencing-by-synthesis, further comprising: before the step b), contacting the solid support having the nucleic acid molecules immobilized thereon with the sequencing primers, so that the sequencing primers hybridize to the nucleic acid molecule on the solid support.

13. The method according to claim 11, wherein the one or more reaction solutions of the step b) comprise a solution containing a polymerase, a labeled nucleotide, or a mixture thereof, provided that the solid support is in contact with each of the and polymerase and the labeled nucleotide, and wherein the signal on the solid support is generated by the labeled nucleotide that complementarily binds to the nucleic acid molecule on the solid support, the labeled nucleotide is polymerized to a 3' end of the sequencing primers via the polymerase using the nucleic acid molecule on the solid support as a template, optionally, the regeneration solution of the step d) comprises a reagent capable of removing a label from the labeled nucleotide, optionally, the labeled nucleotide further comprises a 3' blocking group.

14. The method according to claim 1, wherein the washing is performed by immersing the solid supports in a reaction container containing a washing solution.

15. The method according to claim 1, further comprising: adding a humectant, to the one or more reaction solutions of the step b), the regeneration solution of the step d) and/or the washing solution of the step e).

16. The method according to claim 1, further comprising: optimizing a motion speed of the solid supports between the reaction containers so as to minimize the time that the solid supports are exposed to air.

17. The method according to claim 1, further comprising: adding a reagent, to the one or more reaction solutions in the step b), the regeneration solution in the step d) and/or the washing solution in the step e) so as to retain the reaction solution and/or the washing solution remaining on the solid supports thereon when the solid supports are taken out from the reaction solution and/or the washing solution.

18. The method according to claim 1, further comprising: using a temperature control device to adjust the temperature in each of the reaction containers.

19. The method according to claim 1, wherein during optionally repeating the steps b) to e) in the procedure of the step f), the one or more reaction solutions of the step b) and/or the regeneration solution of the step d) are replaced or not upon each repeating, optionally, when the one or more reaction solutions in the step b) have a reaction temperature of below about 55° C., the time interval for replacing the one or more reaction solutions in the step b) is less than about 8 hours, optionally, when the one or more reaction solutions in the step b) have a reaction temperature of below about 45° C., the time interval for replacing the one or more reaction solutions in the step b) is less than about 24 hours.

\* \* \* \* \*